United States Patent
Wang et al.

(10) Patent No.: US 12,216,071 B2
(45) Date of Patent: Feb. 4, 2025

(54) QUANTITATIVE CHARACTERIZATION OF ALGAL BIOMASS BIOMOLECULES

(71) Applicant: ExxonMobil Technology and Engineering Company, Annandale, NJ (US)

(72) Inventors: Hao Wang, Clinton, NJ (US); Chengrong Wang, Easton, PA (US); Amy C Clingenpeel, Washington, NJ (US); Kuangnan Qian, Skillman, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 515 days.

(21) Appl. No.: 17/142,601

(22) Filed: Jan. 6, 2021

(65) Prior Publication Data

US 2021/0255125 A1   Aug. 19, 2021

Related U.S. Application Data

(60) Provisional application No. 62/978,440, filed on Feb. 19, 2020.

(51) Int. Cl.
| | |
|---|---|
| G01N 24/08 | (2006.01) |
| A01G 33/00 | (2006.01) |
| C11B 1/10 | (2006.01) |
| C12Q 1/02 | (2006.01) |
| C12Q 1/06 | (2006.01) |

(52) U.S. Cl.
CPC ............ *G01N 24/087* (2013.01); *A01G 33/00* (2013.01); *C11B 1/10* (2013.01); *C12Q 1/02* (2013.01); *C12Q 1/06* (2013.01); *G01N 24/08* (2013.01); *G01N 2333/405* (2013.01)

(58) Field of Classification Search
None
See application file for complete search history.

(56) References Cited

PUBLICATIONS

Patel et al., "Lipids detection and quantification in oleaginous microorganisms: an overview of the current state of the art", BMC Chemical Engineering, vol. 1(13), pp. 1-25. (Year: 2019).*
Elliott et al., "Process development for hydrothermal liquefaction of algae feedstocks in a continuous-flow reactor", Algal Research, vol. 2, pp. 445-454. (Year: 2013).*
Marrone et al., "Review of the harvesting and extraction program within the National Alliance for Advanced Biofuels and Bioproducts", Algal Research, vol. 33, pp. 470-485. (Year: 2018).*
Escorsim et al., "Extraction of Acutodesmus obliquus lipids using a mixture of ethanol and hexane as solvent", Biomass and Bioenergy, vol. 108, pp. 470-478. (Year: 2018).*
Mallick et al., "Progress and Challenges in Microalgal Biodiesel Production", Frontiers in Microbiology, vol. 7, Article 1019, pp. 1-11. (Year: 2016).*
Zhang et al., "Biosorption of nonylphenol by pure algae, field-collected planktons and their fractions", Environmental Pollution, vol. 198, pp. 61-69. (Year: 2015).*
Akhter et al., "Identification of aquatically available carbon from algae through solution-state NMR of whole 13C-labelled cells", Analytical and Bioanalytical Chemistry, vol. 408, pp. 4357-4370. (Year: 2016).*
Molina Grima, et al., "Recovery of microalgal biomass and metabolites: process options and economics", Biotechnology Advances, vol. 20, pp. 491-515. (Year: 2003).*
Huang et al., "Micro-Raman Spectroscopy of Algae: Composition Analysis and Fluorescence Background Behavior", Biotechnology and Bioengineering 105(5), 2010, pp. 889-898.
Hena et al., "Cultivation of algae consortium in a dairy farm wastewater for biodiesel production", Water Resources and Industry 10, 2015, pp. 1-14.
Pistorius et al., Monitoring of Biomass Composition From Microbiological Sources by Means of FT-IR Spectroscopy, Biotechnology and Bioengineering 103(1), 2009, pp. 123-129.
Davey et al., "Rapid triacylglyceride detection and quantification in live micro-algal cultures via liquid state 1H NMR", Algal Research 1, 2012, pp. 166-175.

* cited by examiner

*Primary Examiner* — Michelle F. Paguio Frising
*Assistant Examiner* — Grant C Currens
(74) *Attorney, Agent, or Firm* — Shook, Hardy & Bacon L.L.P.

(57) ABSTRACT

A method and system for direct quantification of the concentration of biomolecules in algal biomass. The biomolecules include lipids, proteins, and carbohydrates. An algae slurry is cultivated within a cultivation vessel, and algal biomass is harvested therefrom. A portion of biomass is analyzed using solvent-lipid analysis to extract lipids and nuclear magnetic resonance spectroscopy is used to quantify the biomolecular concentration of the biomass.

13 Claims, 1 Drawing Sheet

QUANTITATIVE CHARACTERIZATION OF ALGAL BIOMASS BIOMOLECULES

CROSS-REFERENCE TO RELATED APPLICATIONS

This application is related to and claims the benefit of priority from U.S. Provisional Application No. 62/978,440 filed Feb. 19, 2020, which is hereby incorporated by reference in its entirety.

FIELD OF THE INVENTION

This application relates to algal biomass processing and, more particularly, to quantitative characterization of algal biomass biomolecules.

BACKGROUND OF THE INVENTION

Concerns about climate change, carbon dioxide ($CO_2$) emissions, and depleting oil and gas resources have led to widespread interest in the production of biofuels from algae, including microalgae. As compared to other plant-based feedstocks, algae have higher $CO_2$ fixation efficiencies and growth rates, and growing algae can efficiently utilize wastewater, biomass residue, and industrial gases as nutrient sources.

Algae are photoautotrophic organisms that can survive, grow, and reproduce with energy derived entirely from the sun through the process of photosynthesis. Photosynthesis is the process used by plants, algae, and certain bacteria to capture $CO_2$, harness energy from sunlight, and turn them into gaseous oxygen, carbohydrate, and other compounds critical to life of the plant and algae.

To produce algal biomass, algae cells are generally grown in a water slurry comprising water and nutrients. The algae may be cultivated in indoor or outdoor environments, and in closed or open cultivation systems. Closed cultivation systems include photobioreactors, which utilize natural or artificial light to grow algae in an environment that is generally isolated from the external atmosphere. Such photobioreactors may be in a variety of shaped configurations, but are typically tubular or flat paneled. Open cultivation systems include natural and artificial ponds that utilize sunlight to facilitate photosynthesis. Artificial ponds are often shaped in circular or raceway-shaped (oval) configurations.

Various processing methods exist for harvesting cultivated algal biomass to extract lipids therefrom for the production of fuel and other oil-based products. Moreover, harvesting cultivated algal biomass can be used to produce non-fuel or non-oil-based products, including nutraceuticals, pharmaceuticals, cosmetics, chemicals (e.g., paints, dyes, and colorants), fertilizer and animal feed, and the like. Accordingly, the composition of a particular algal biomass is paramount to understanding and optimizing desirable biomolecules for use in forming one or more types of products derived from the biomass.

SUMMARY OF THE INVENTION

This present disclosure relates to algal biomass processing and, more particularly, to quantitative characterization of algal biomass biomolecules.

In some aspects, a method is disclosed that includes the steps of harvesting algal biomass from a cultivated algae water slurry. Lipids are extracted from at least a portion of the harvested algal biomass using solvent-lipid extraction. Thereafter, the biomolecular concentration of the algal biomass is quantified using nuclear magnetic resonance spectroscopy.

In some aspects, a method is disclosed that includes the steps of harvesting algal biomass from a cultivated algae water slurry. Lipids are extracted from at least a portion of the algal biomass using solvent-lipid extraction, thereby producing a first lipids-containing fraction and a second lipids-free fraction, the lipids-free fraction comprising protein and carbohydrates. Thereafter, a sample of the portion of the algal biomass and a sample of the lipids-free fraction are analyzed using nuclear magnetic resonance spectroscopy to quantify a concentration of lipids, protein, and carbohydrates of the algal biomass.

In some aspects, a system is disclosed that includes a harvesting system for harvesting algal biomass from a cultivated algae water slurry, a solvent-lipid extractor for extracting lipids from a portion of the algal biomass, and a nuclear magnetic resonance spectrometer for quantifying biomolecular concentration of the algal biomass.

BRIEF DESCRIPTION OF THE DRAWINGS

The following figures are included to illustrate certain aspects of the present disclosure, and should not be viewed as exclusive examples. The subject matter disclosed is capable of considerable modifications, alterations, combinations, and equivalents in form and function, without departing from the scope of this disclosure.

DETAILED DESCRIPTION OF THE INVENTION

Figure 1:
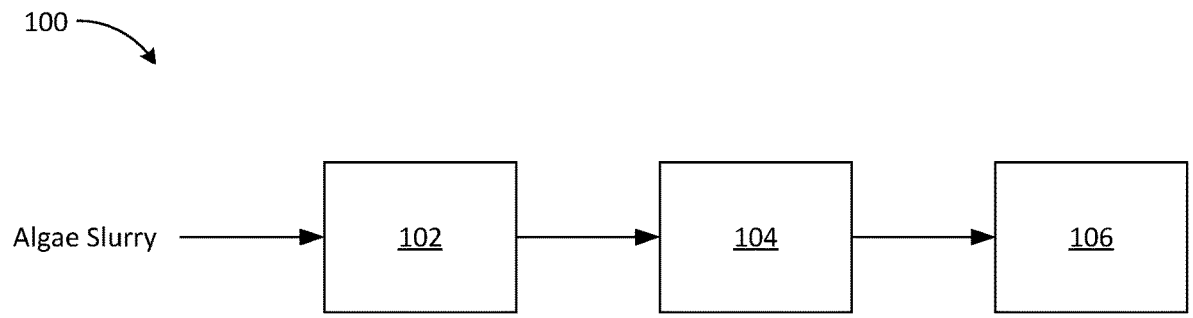
FIG. 1 illustrates an example system that may be used to grow and harvest algae for biofuel production according to various aspects of the present disclosure.

This present disclosure relates to algal biomass processing and, more particularly, to quantitative characterization of algal biomass biomolecules, including lipids, proteins, and carbohydrates.

Biofuel production from harvested algal biomass derived from cultivated algae slurries offers sustainable energy solutions to reduce reliance on fossil fuels and reduce greenhouse gas emissions. The biomolecular composition of harvested algal biomass is vital for understanding growth, recovery, and processing parameters required to produce useful commercial products. Moreover, knowledge of the biomolecular composition of a biomass can be used to manipulate the composition of an algae slurry to maximize or increase lipid production, thereby resulting in increased biofuel yield. However, quantitative determination of the complex biomolecular composition of algal biomass has been heretofore challenging, requiring indirect methods that often lead to results that cannot be fully mass balanced or carbon balanced.

The present disclosure advantageously provides a direct and quantitative approach for determining the biomolecular composition of harvested algal biomass, including total proteins, carbohydrates (including cellulosic content), and lipids (including chlorophyll). As used herein, the term "chlorophyll," and grammatical variants thereof, encompasses non-modified and modified chlorophyll biomolecules (e.g., demetallated chlorophyll), including biomolecules comprising long alkyl chain lengths (>C6), and any combination thereof. The approach utilizes a combination of solvent-lipid extraction (e.g., Soxhlet extraction) and nuclear magnetic resonance (NMR) spectroscopy. The approach differs from previous methods utilized to characterize biomolecular components of algal biomass, which were indirect methods that required digestion of algae cells, often leading to inaccurate or incomplete results that do not encompass total concentration for the aforementioned biomolecules. For example, prior methods for determining biomolecular concentration of algae required converting the biomass into their building blocks for analysis. Protein would be completely hydrolyzed and then subjected to chromatographic analysis (e.g., high performance liquid chromatography) against amino acid standards. Carbohydrates would be digested into sugar monomers by aggressive chemical reaction, followed by ion chromatography analysis. And lipids would be characterized by converting to fatty acid methyl esters and then analyzed by gas chromatography. These indirect methods are costly, time consuming, and, as stated above, often cannot be fully mass balanced or carbon balanced. Differently, the approach provided in the present disclosure first extracts total lipids and chlorophylls using solvent-lipid extraction (i.e., extraction of lipids utilizing a solvent, resulting in a lipids-free and lipids-containing fraction) and thereafter analyzes both the extracted lipids-free fraction and initial biomass by NMR spectroscopy, using an NMR spectrometer, to quantify total carbons from proteins and carbohydrates and derive total lipids. This direct and quantitative approach is accurate, requires relatively short processing time, is relatively less costly compared to prior methods, and does not require digestion of biomass.

It will be appreciated that while the methods and systems described herein are made with reference to algal biomass, they may be equally applicable to other types of biomass containing one or more of lipids, proteins, and carbohydrates, whose concentrations are of interest. That is, any biomass derived from organic matter may be treated according to the present disclosure for determination of biomolecular concentration including, but not limited to, biomass derived from wood, crops, animal waste, solid waste, landfill gas, biogas, and any combination thereof.

Referring first to FIG. 1, illustrated is an example system 100 that may be used to grow and harvest algae for biofuel production in various aspects of the present disclosure. As illustrated, the system 100 includes cultivation vessel 102. As used herein, the term "cultivation vessel," and grammatical variants thereof, refers to any of an open or closed cultivation system used for the growth of algal biomass, including photobioreactors, natural ponds, artificial ponds (e.g., raceway ponds), and the like. The cultivation vessel is fed and contains an algae slurry for cultivation (growth). Of note, the size of the cultivation vessel for use in the aspects of the present disclosure may be commercial in size or otherwise much smaller laboratory sized (e.g., for experimentation prior to large scale cultivation).

As used herein, the term "algae slurry," and grammatical variants thereof, refers to a flowable mixture comprising at least water, algae cells, and algae nutrient media (e.g., phosphorous, nitrogen, and optionally additional elemental nutrients). The order of addition of the components of the algae slurry into a cultivation vessel is not considered to be particularly limiting, and may be included in any order. In some aspects, the algae cells are in the form of a pre-grown "seed stock" to increase algae concentration in smaller vessel(s) prior to formation of the full volume of the algae slurry, without departing from the scope of the present disclosure.

Algae cell sources for the preparing the algae slurry include, but are not limited to, unicellular and multicellular algae. Examples of such algae may include, but are not limited to, a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae may be of the classes Chlorophyceae and/or Haptophyta Haptophyta. Specific species may include, but are not limited to, *Neochloris oleoabundans, Scenedesmus dimorphus, Euglena gracilis, Phaeodactylum tricomutum, Pleurochrysis carterae, Prymnesium parvum, Tetraselmis chui*, and *Chlamydomonas reinhardtii*. Additional or alternate algal sources may include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Emodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinabum, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

The water for use in preparing the algae slurry may be from any water source including, but not limited to, fresh water, brackish water, seawater, wastewater (treated or untreated), synthetic seawater, and any combination thereof. The wastewater may derive, for example, from previously cultivated algae slurries after separation and removal of the algae components. The synthetic seawater may, for example, be prepared by dissolving salts into fresh water.

The algae nutrient media for use in forming an algae slurry may comprise at least nitrogen (e.g., in the form of ammonium nitrate or ammonium urea) and phosphorous. Other elemental micronutrients may also be included, such as potassium, iron, manganese, copper, zinc, molybdenum, vanadium, boron, chloride, cobalt, silicon, and the like, and any combination thereof.

With continued reference to FIG. 1, the algae slurry may be contained in the cultivation vessel 102 for a predetermined amount of time or until the algae within the algae slurry matures and is ready for harvesting. Typical residence time in the cultivation vessel 102, for example, may range between about 2 days and about 20 days. Once the algae matures and is otherwise ready for harvesting, the now-cultivated algae slurry is extracted from the cultivation vessel 102 and pumped to one or more harvesting systems 104 to be harvested and dewatered/desalted, during which the algae in cultivated algae slurry is generally separated from the water and, in various aspects, further dried (e.g., via heat exchanges, air dryers, freeze dry (or lyophilized), and the like, and any combination thereof). As used herein, the term "harvesting system," and grammatical variants thereof, refers to refers to any equipment or equipment system that can be used to selectively harvest (separate) algal biomass (cultivated algae cells) from an algae slurry. Generally, the harvesting system(s) described herein comprise one or more components to achieve desired harvesting of a concentrated algal biomass. The harvesting system(s) 104 may comprise any separator (e.g., skimmer, centrifuge, and the like), filter, air sparger, pump, or dewatering system, dialysis, and the like, and any combination thereof.

The cultivated, separated (harvested) algae is then conveyed downstream for lipid extraction 106 in preparation for biofuel production. In one or all aspects, the separated water can be purged from system 100 (e.g., at or downstream of the harvesting system(s) 104) via a blowdown stream and discharged into the environment or reused for another application. In one or more aspects, the separated water purged via the blowdown stream may be conveyed to a wastewater treatment plant for treatment so that the separated water can be discharged into the environment with minimal impact.

A portion of the cultivated, separated algae (the "biomass") obtained from the harvesting system(s) 104 may be characterized in terms of biomolecular concentration according to the methods and systems of the present disclosure. This characterization may be performed before or after lipid extraction and biofuel production. For example, in some aspects, characterization of a portion of the algal biomass may be used to tailor algae slurry composition to optimize growth and lipid production for future slurry growth (e.g., using the same algae type). That is, knowledge of the biomolecular composition of the biomass may be used to adjust, for example, the predetermined cultivation time, the components and amount of each of the components forming the algae nutrients within the slurry, the volume or concentration of algae cells required at one or more times during cultivation, and the like, and any combination thereof. In alternative or additional aspects, characterization of a portion of the algal biomass may be used to tailor the particular lipid extraction techniques (e.g., chemical (solvent) extraction, mechanical extraction, and combinations thereof) to maximize lipid obtention therefrom.

As described herein, a portion of the cultivated and separated algal biomass may be initially analyzed using solvent-lipid extraction analysis to remove total lipid content (including chlorophyll) from the biomass. As such, the remaining lipid-free biomass comprises all protein and carbohydrate biomolecular content, which may then be further analyzed without interference from lipids. The lipid-free biomass and original biomass may then be analyzed and compared using NMR to quantify total carbons from the proteins and carbohydrates, and derive total lipids. That is, the direct and quantitative approach for determining the biomolecular composition of an algal biomass according to the present disclosure is a two-step approach.

The portion of the algal biomass used in the two-step approach is in solid form, which may be milled or otherwise reduced in cell size, and in some aspects may be lyophilized, fully dewatered, or otherwise dehydrated, prior to analysis. In some instances, the first step of the two-step approach, the solvent-lipid extraction step, may utilize algal biomass having a moisture content of less than about 20% by weight (e.g., in a paste form) to about 0% (including 0%), encompassing any value and subset therebetween. During the extraction step, the moisture content will be reduced to substantially 0% (or 0%), noting that due to ambient exposure, some moisture may remain. Accordingly, the moisture content of the algal biomass for use in the second step of the two-step approach, the NMR step, is equal to or substantially 0%. In some aspects, the algal biomass may be freeze dried, vacuum dried, heat dried, and the like, and any combination thereof. The specific amount of the portion of algal biomass used in the two-step approach is not considered to be particularly limiting, provided it is in sufficient quantity to obtain accurate biomolecular concentration information according to the present disclosure, and is generally dictated by the instrumentation used to perform the approach (e.g., sample chambers may differ in size depending on the selected instrumentation). The particular amount of biomass analyzed may be dependent on various factors including, but not limited to, the type and capacity of the analytical instrumentation used, the availability of algal biomass sample, and the like, and any combination thereof.

The initial analysis of the disclosed two-step approach may include any solvent-lipid extraction method suitable for separating lipids (including chlorophyll) from a biomass sample (e.g., from proteins and carbohydrates within the biomass sample) using a solvent, such as static extraction (e.g., Bligh and Dyer extraction), gravitational extraction, solvent reflux extraction (e.g., Soxhelet extraction), and the like, and any combination thereof. In various aspects, the initial analysis of the disclosed two-step approach may include solvent-lipid extraction based on solvent reflux and siphon principles to continuously extract lipids from solid algal biomass (which may be lyophilized). In one or all aspects, the solvent-lipid extraction may be performed utilizing a Soxhlet extractor. The solvent used in the solvent-lipid extraction (e.g., Soxhlet extraction) may be any organic solvent capable of extracting lipids from the remaining biomolecules of an algal biomass. The solvent is recycled and continuously flows over the biomass (e.g., one or more hours to many days), wherein lipids are extracted therefrom and the remaining biomass residue comprises lipid-free biomass. Accordingly, the solvent-lipid extraction produces a solvent-soluble fraction (comprising lipids, or a "lipids-containing fraction") and a solvent-insoluble fraction (comprising carbohydrates and proteins, or a "lipids-free fraction").

The organic solvent used in the solvent-lipid extraction described herein may include, but are not limited to, a polar organic solvent, a non-polar organic solvent, and any combination thereof. For example, the organic solvent may be a paraffin solvent, an aromatic solvent, an alcohol solvent (including a chlorinated alcohol solvent), an ester solvent, an ether solvent, and any combination thereof. Examples of suitable specific organic solvents for use in the extraction analysis of the present disclosure include, but are not limited to, ethanol, methanol, butanol, chloroform, n-hexane, acetone, ethyl acetate, toluene, benzene, and any combination thereof. As used herein, the term "organic solvent," and grammatical variants thereof, refers to pure or otherwise diluted solvents (e.g., 95% ethanol in water).

The extracted solvent-insoluble fraction of the two-step approach described herein and the original biomass (e.g., a portion of the total lyophilized biomass that was used in the extraction process) are analyzed using NMR spectroscopy and compared to determine total concentration of lipids (and chlorophyll), proteins, and carbohydrates in said original biomass. NMR spectroscopy is an analytical technique based on electromagnetic field and atomic nuclear spin. The resultant NMR spectra displays a plot of intensity versus chemical shift (parts per million or "ppm"), and known ranges within said spectra are correlative to particular carbon compounds (functional groups).

In preferred embodiments, the solid state NMR used in accordance with the two-step approach of the present disclosure is solid state NMR, such as 13C solid state NMR. 13C NMR is the application of NMR to carbon, and particularly useful in identifying the carbon-containing organic biomolecules in biomass. Sample preparation, probe selection, and the like for performing the NMR is not considered to be particularly limited and is considered a routine undertaking for those of ordinary skill in the art having benefit of this disclosure.

For example, 13C chemical shifts representing compounds (functional groups) within the biomolecules of interest in biomass may be within about ("~") the ranges in Table 1 below, which includes the types of biomolecules in which they may be found. Other carbon-containing compounds (functional groups) may also be evaluated using the systems and methods described herein, without departing from the scope of the present disclosure.

TABLE 1

| Compound | $^{13}$C NMR Range (ppm) | Biomass Biomolecule(s) |
| --- | --- | --- |
| O—C=O (Carboxyl Carbons) | ~186-~163 | Protein, Lipid, Chlorophyll |
| C=C (Unsaturated Carbons) | ~145-~110 | Lipid, Chlorophyll |
| C—O—C (Bridging Ether Carbons) | ~145-~110 | Carbohydrate |
| C—O (Oxygenated Carbons) | ~110-~44 | Carbohydrate, Lipid |
| CH, CH$_2$, CH$_3$ (Paraffinic Carbons) | ~44-~5 | Protein, Lipid, Chlorophyll |

The NMR spectra obtained from biomass and the extracted lipids-free fraction according to the two-step approach of the present disclosure are compared and, using calculations based on average carbon molecular weight, the total amount of lipid (including chlorophyll), protein, and carbohydrate can be determined, as illustrated in the Example hereinbelow.

Accordingly, the systems and methods of the present disclosure advantageously provide direct and quantitative determination of the biomolecular content of biomass, including cultivated algal biomass for use in optimizing growth conditions and downstream processing (e.g., lipid extraction) methods for deriving materials used in the development of commercial products, such as biofuels.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the examples of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative examples incorporating the aspects of the present disclosure are presented herein. Not all features of a physical implementation are described or shown in this application for the sake of clarity. It is understood that in the development of a physical embodiment incorporating the aspects of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

EMBODIMENTS LISTING

The present disclosure provides, among others, the following embodiments, each of which may be considered as optionally including any alternate embodiments.

Clause 1. A method comprising: harvesting algal biomass from a cultivated algae water slurry; extracting lipids from a portion of the algal biomass using solvent-lipid extraction; and quantifying biomolecular concentration of the algal biomass using nuclear magnetic resonance spectroscopy.

Clause 2. The method of Clause 1, wherein the biomolecular concentration comprises lipids, protein, and carbohydrates.

Clause 3. The method of Clause 2, wherein the lipids include chlorophyll.

Clause 4. The method of any of the preceding Clauses, wherein the solvent-lipid extraction is Soxhlet extraction using an organic solvent.

Clause 5. The method of Clause 4, wherein the organic solvent comprises a polar organic solvent, a non-polar organic solvent, and any combination thereof.

Clause 6. The method of Clause 4 or 5, wherein the organic solvent is comprises ethanol.

Clause 7. The method of any of the preceding Clauses, wherein the nuclear magnetic resonance spectroscopy is 13C solid state nuclear magnetic resonance spectroscopy.

Clause 9. The method of any of the preceding Clauses, further comprising lyophilizing the portion of the algal biomass.

Clause 10. A method comprising: harvesting algal biomass from a cultivated algae water slurry; extracting lipids from a portion of the algal biomass using solvent-lipid extraction, wherein the solvent-lipid extraction produces a first lipids-containing fraction and a second lipids-free fraction, the lipids-free fraction comprising protein and carbohydrates; and analyzing a sample of the portion of the algal biomass and a sample of the lipids-free fraction using nuclear magnetic resonance spectroscopy to quantify a concentration of lipids, protein, and carbohydrates of the algal biomass.

Clause 11. The method of Clause 10, further comprising lyophilizing the portion of the algal biomass.

Clause 12. The method of Clause 10 or 11, wherein the lipids include chlorophyll.

Clause 13. The method of Clauses 10 to 12, wherein the solvent-lipid extraction is Soxhlet extraction using an organic solvent.

Clause 14. The method of Clause 13, wherein the organic solvent wherein the organic solvent comprises a polar organic solvent, a non-polar organic solvent, and any combination thereof.

Clause 15. The method of Clause 13 or 14, wherein the organic solvent comprises ethanol.

Clause 16. The method of Clauses 10 to 15, wherein the nuclear magnetic resonance spectroscopy is 13C solid state nuclear magnetic resonance spectroscopy.

Clause 17. A system comprising: a harvesting system for harvesting algal biomass from a cultivated algae water slurry; a solvent-lipid extractor for extracting lipids from a portion of the algal biomass; and a nuclear magnetic resonance spectrometer for quantifying biomolecular concentration of the algal biomass.

Clause 18. The system of Clause 17, wherein the biomolecular concentration comprises lipids, protein, and carbohydrates.

Clause 19. The system of Clause 18, wherein the lipids include chlorophyll.

Clause 20. The system of Clauses 17 to 19, wherein the solvent-lipid extraction is Soxhlet extraction using an organic solvent.

Clause 21. The system of Clause 20, wherein the organic solvent comprises a polar organic solvent, a non-polar organic solvent, and any combination thereof.

Clause 22. The system of Clause 20 or 21, wherein the organic solvent is comprises ethanol.

Clause 23. The system of Clauses 17 to 22, wherein the nuclear magnetic resonance spectroscopy is 13C solid state nuclear magnetic resonance spectroscopy.

To facilitate a better understanding of the embodiments of the present invention, the following example of a preferred or representative example is given. In no way should the following example be read to limit, or to define, the scope of the disclosure.

EXAMPLE

In this example, four samples of separated algal biomass were obtained from actual biomass cultivated in outdoor cultivation vessels. Each of the four samples are of the same type of algae, but harvested at different growth stages. These samples are represented as S1, S2, S3, and S4 in the description hereinbelow. S1 and S2 include biomass cultivated in nitrogen-replete conditions (i.e., nitrogen is available) and S3 and S4 include biomass cultivated in nitrogen-deplete conditions (i.e., nitrogen is unavailable), for comparison. Nitrogen (nutrient typically included in an algae slurry) is generally considered a "lipid trigger" to increase or otherwise optimize lipid production during cultivation of an algae slurry.

The S1, S2, S3, and S4 biomass samples were initially lysed and lyophilized. The initial solvent-lipid extraction was performed using a standard Soxhlet extractor of each of the biomass samples (separately) and with ethanol as the solvent. Collected from the extractor was the ethanol-soluble fraction comprising lipids and the ethanol-insoluble fraction comprising proteins and carbohydrates (or the "Residue"). The Residue fractions are represented as S1-Res, S2-Res, S3-Res, and S4-Res for each of S1, S2, S3, and S4, respectively, in the description hereinbelow. In this example, the ethanol-soluble fraction was further partitioned to provide a C7+ asphaltene fraction, which formed a majority portion of the ethanol-soluble fraction, and an insoluble fraction.

The weight percentage of the Residue fraction for each sample compared to the ethanol-insoluble fraction is provided in Table 2 below.

TABLE 2

| Sample | S1 | S2 | S3 | S4 |
|---|---|---|---|---|
| Residue % | 80.41% | 83.17% | 74.62% | 78.70% |

As shown in Table 2, the Residue comprises a large portion of the material from the solvent-lipid extraction step, further emphasizing the importance of characterizing biomolecular biomass to optimize lipid production (noting that weight of biomolecules are not equivalent; see Table 4 for actual concentrations).

Figure 2:
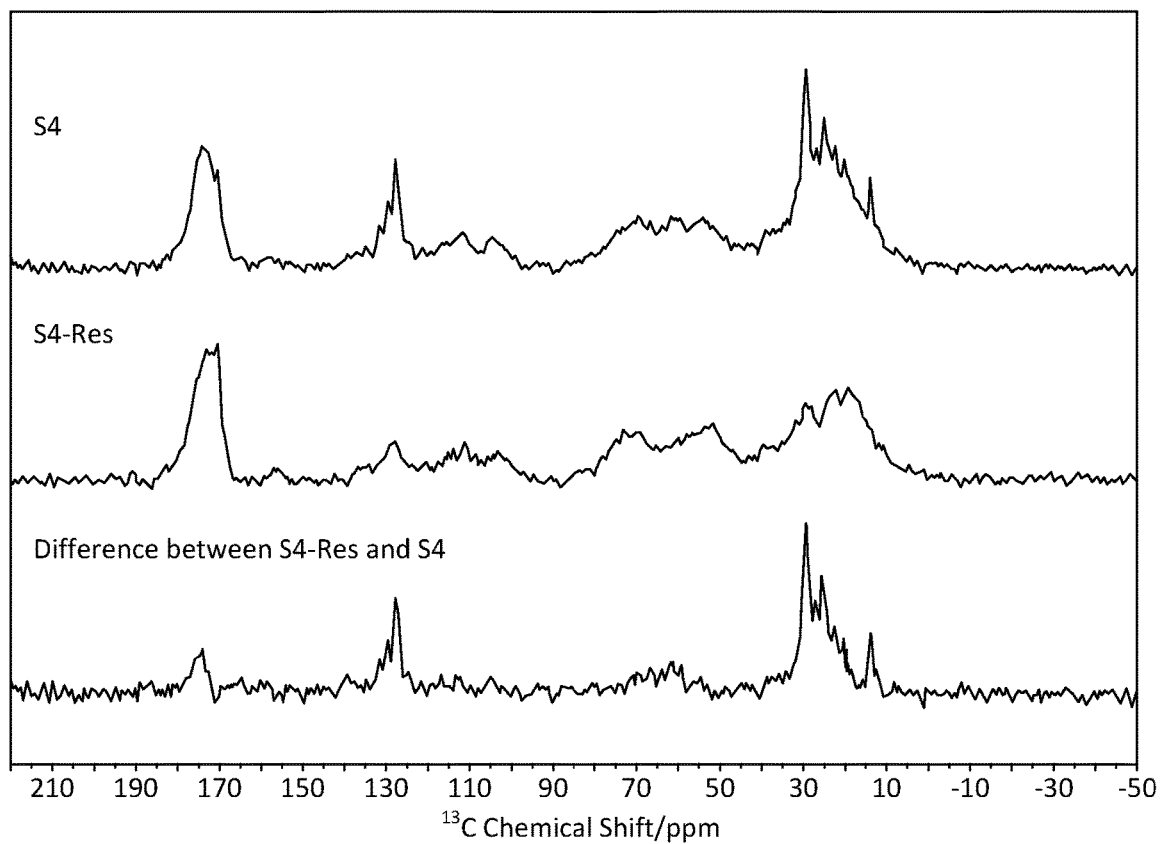
FIG. 2 illustrates an example of 13C NMR spectra for use in quantitative characterization of algal biomass biomolecules according to various aspects of the present disclosure.

13C NMR spectroscopy was conducted on the original 51, S2, S3, and S4 samples, as well as the S1-Res, S2-Res, S3-Res, and S4-Res samples for quantification. The resultant NMR spectra were analyzed by pairing and comparing each spectra for S1 and S1-Res; S2 and S2-Res; S3 and S3-Res; and S4 and S4-Res. As a representative example, FIG. 2 illustrates a spectral plot pairing for S4 (top) and S4-Res (middle), including a normalized plot (bottom) representing the spectral difference between the S4 and S4-Res plots. The normalized plot accordingly represents the lipid content of the algal biomass being examined.

Based on Table 1 above and in view of the 13C NMR spectra obtained in this example, the following biomolecular assignments were assigned to the lyophilized biomass NMR plots (S1, S2, S3, and S4), the Residue Fraction NMR plots (S1-Res, S2-Res, S3-Res, and S4-Res), and the difference NMR plots ("Difference"). The assignments are shown in Table 3 below.

TABLE 3

| $^{13}$C NMR (ppm) | 186-163 | 145-110 | 110-45 | 44-5 |
|---|---|---|---|---|
| Lyophilized Biomass | Protein, Lipid, Chlorophyll | Lipid, Chlorophyll, Carbohydrate | Lipid, Carbohydrate | Protein, Lipid, Chlorophyll |
| Residue Fraction | Protein | Carbohydrate | Carbohydrate | Protein |
| Difference | Lipid, Chlorophyll | Lipid, Chlorophyll | Lipid | Lipid, Chlorophyll |

Evaluation of the NMR spectra based on Table 3 and the known carbon molecular weight, the following mole % concentrations of total lipid (including chlorophyll), protein, and carbohydrates were calculated, as shown in Table 4 below.

TABLE 4

| Sample | Lipid (Chlorophyll) | Protein | Carbohydrate |
|---|---|---|---|
| S1 | 38.5% | 46.4% | 15.0% |
| S2 | 35.6% | 45.8% | 18.6% |
| S3 | 34.7% | 42.6% | 22.7% |
| S4 | 41.4% | 40.5% | 18.1% |

Accordingly, the present disclosure advantageously provides a direct and quantitative method for determination of total biomolecules of interest that is simplified, cost effective, and more accurate compared to prior methodologies.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method comprising:
    harvesting algal biomass from a cultivated algae water slurry;
    extracting lipids from a portion of the algal biomass using solvent-lipid extraction, wherein the solvent-lipid extraction produces a lipids-containing fraction and a lipids-free fraction, the lipids-free fraction comprising protein and carbohydrates;
    quantifying a first biomolecular concentration of a first carbon-containing compound in the lipids-free fraction using nuclear magnetic resonance spectroscopy;
    quantifying a second biomolecular concentration of a second carbon-containing compound in the algal biomass using nuclear magnetic resonance spectroscopy;
    determining a total amount of a lipid, protein, and carbohydrate in the algal biomass by comparing, at least, the first biomolecular concentration with the second biomolecular concentration; and
    tailoring, based on the total amount of lipid, protein, and carbohydrate in the algal biomass of the cultivated algae water slurry, the total amount of lipid, protein, and carbohydrate of a subsequently cultivated algae water slurry by adjusting a predetermined cultivation time of the subsequently cultivated algae water slurry.

2. The method of claim 1, wherein the first carbon-containing compound is a protein.

3. The method of claim 2, wherein the second carbon-containing compound is a carbohydrate.

4. The method of claim 1, wherein the solvent-lipid extraction is Soxhlet extraction using an organic solvent.

5. The method of claim 3, further comprising calculating a mole percent concentration for each of total lipid, protein, and carbohydrate in the algal biomass.

6. The method of claim 4, wherein the organic solvent comprises ethanol.

7. A method comprising:
    harvesting algal biomass from a cultivated algae water slurry;
    extracting lipids from a portion of the algal biomass using solvent-lipid extraction, wherein the solvent-lipid extraction produces a lipids-containing fraction and a lipids-free fraction, the lipids-free fraction comprising protein and carbohydrates;
    analyzing an original sample of the algal biomass using nuclear magnetic resonance spectroscopy to generate a first spectral plot;
    analyzing a sample of the lipids-free fraction portion using nuclear magnetic resonance spectroscopy to generate a second spectral plot;
    determining a percent concentration for each of total lipid, protein, and carbohydrate in the algal biomass by generating, at least a spectral difference between the first spectral plot and the second spectral plot; and
    tailoring, based on the percent concentration for each of total lipid, protein, and carbohydrate in the algal biomass of the cultivated algae water slurry, the percent concentration of each of total lipid, protein, and carbohydrate in a subsequently cultivated algae water slurry by any one or more of: adjusting a predetermined cultivation time of the subsequently cultivated algae water slurry, adjusting an amount of a nutrient within the subsequently cultivated algae water slurry, or adjusting a concentration of algae cells during cultivation at one or more times.

8. The method of claim 7, further comprising lyophilizing the portion of the algal biomass prior to extracting lipids from the portion of the algae biomass, and wherein the original sample of the algal biomass is lyophilized prior to analyzing the original sample of the algal biomass using nuclear magnetic resonance spectroscopy.

9. The method of claim 7, wherein the percent concentration for each of total lipid, protein, and carbohydrate are tailored by adjusting the amount of the nutrient within the second cultivated algae water slurry.

10. The method of claim 7, wherein the solvent-lipid extraction is Soxhlet extraction using an organic solvent.

11. The method of claim 10, wherein the organic solvent wherein the organic solvent comprises a polar organic solvent, a non-polar organic solvent, and any combination thereof.

12. The method of claim 10, wherein the organic solvent comprises ethanol.

13. The method of claim 7, wherein the nuclear magnetic resonance spectroscopy is 13C solid-state nuclear magnetic resonance spectroscopy.

* * * * *